(12) United States Patent
Rault et al.

(10) Patent No.: US 8,853,276 B2
(45) Date of Patent: Oct. 7, 2014

(54) GUANIDINE DERIVATIVES IN CINNAMIC SERIES

(75) Inventors: Sylvain Rault, Moult (FR); Jean Charles Lancelot, Tour en Bessin (FR); Peggy Suzanne, Mondeville (FR); Anne-Sophie Voisin-Chiret, Bernieres-sur-mer (FR); Regis Pecquet, Mennecy (FR); Jean-Christophe Joseph, Morsang sur Orge (FR)

(73) Assignee: Produits Chimiques Auxiliaires et de Synthese, Longjumeau (FR)

( * ) Notice: Subject to any disclaimer, the term of this patent is extended or adjusted under 35 U.S.C. 154(b) by 0 days.

(21) Appl. No.: 13/821,093

(22) PCT Filed: Sep. 6, 2011

(86) PCT No.: PCT/FR2011/052035
§ 371 (c)(1),
(2), (4) Date: Mar. 6, 2013

(87) PCT Pub. No.: WO2012/032257
PCT Pub. Date: Mar. 15, 2012

(65) Prior Publication Data
US 2013/0165507 A1 Jun. 27, 2013

(30) Foreign Application Priority Data
Sep. 7, 2010 (FR) .................... 10 57087

(51) Int. Cl.
*A01N 37/52* (2006.01)
*A61K 31/155* (2006.01)
*C07C 281/00* (2006.01)
*C07C 281/16* (2006.01)
*C07C 279/00* (2006.01)
*C07D 249/18* (2006.01)
*A61K 8/43* (2006.01)
*C07D 317/46* (2006.01)
*A61Q 19/08* (2006.01)
*C07C 243/34* (2006.01)
*C07C 277/08* (2006.01)
*C07C 243/32* (2006.01)

(52) U.S. Cl.
CPC ............. *C07C 281/16* (2013.01); *C07C 279/00* (2013.01); *C07D 249/18* (2013.01); *A61K 8/43* (2013.01); *C07D 317/46* (2013.01); *A61Q 19/08* (2013.01); *C07C 243/34* (2013.01); *C07C 277/08* (2013.01); *C07C 243/32* (2013.01)
USPC .......................................... 514/632; 564/227

(58) Field of Classification Search
CPC ..................... A61K 31/155; C07C 243/18
USPC ............................................. 514/632; 564/227
See application file for complete search history.

(56) References Cited

U.S. PATENT DOCUMENTS 2,118,566 A * 5/1938 Miles ........................... 424/601
5,130,324 A 7/1992 Ulrich et al.
5,476,849 A 12/1995 Ulrich et al.

FOREIGN PATENT DOCUMENTS

EP 0 339 496 11/1989

OTHER PUBLICATIONS

Markman et. al., CAS STN, Abstract, publ. 1964.*
CAS STN, Chemical Abstract Services, publ. date Dec. 6, 2010.*
Busev A.I. et al.—"Extraction of the complex of pentavalent molybdenum with thioglycolic acid in the presence of guanidine derivatives."—Journal of Analytical Chemistry of the USSR, Consultants Burea, New York, NY, vol. 20, Jan. 1, 1965—pp. 66-71.
Wang X. et al.—"Features and applications of reactions of alpha-beta-unsaturated N-acylbenzotriazoles with amino compounds"—Tetrahedron, vol. 64, Jun. 30, 2008—pp. 6510-6521.
Pardin C. et al.—"Cinnamoyl Inhibitors of Tissue Transglutaminase"—Journal of Organic Chemistry—vol. 73, Jun. 27, 2008—pp. 5766-5775.
Katritzky A. et al.—"Preperation and Synthetic Applications of N-(alpha, Beta-Unsaturated Acyl)-Alpha-amino Acid Derivatives"—Heterocycles, vol. 77, No. 2, 2009—pp. 1249-1259.
Tanaka K. et al.—"Syntheses and Anti-Inflammatory and Analgesic Activities of Hydroxamic Acids and Hydrazides"—Chemical and Pharmaceutical Bulletin, vol. 31 (1983)—pp. 2810-2819.
Curtius Th et al.—"Uber das Nydrazid der m-Nitrozimsaure und sein Verhalten gegen Salpetrigsaure"—Journal fuer Praktische Chemie, vol. 107, Jan. 1, 1924—pp. 86 and 98.
Flammang M. et al.—"Derives de l'acide cafeique"—Chimica Therapeutica, vol. 4, Jan. 1, 1969—pp. 120-126.
Anzai K. et al.—"Studies on a new antibiotic, Tuberin. V."—The Journal of Antibiotics, vol. 15, Sep. 1, 1962—pp. 202-208.

(Continued)

*Primary Examiner* — Sarah Pihonak
(74) *Attorney, Agent, or Firm* — Gerald E. Hespos; Michael J. Porco; Matthew T. Hespos

(57) ABSTRACT

The invention relates to novel guanidine derivatives in the cinnamic series of general formula (I):

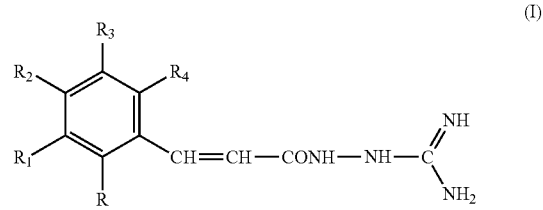

The invention also relates to the process for preparing said guanidine derivatives and also to synthetic intermediates.
Finally, the invention relates to the use of the guanidine derivatives for the preparation of compositions with anti-glycation properties, especially in cosmetology.

8 Claims, No Drawings

(56) References Cited

OTHER PUBLICATIONS

Zhang X. et al.—"A new procedure for preparation of carboxylic acid hydrazides."—Journal of Organic Chemistry, vol. 67, Dec. 4, 2002—pp. 9471-9474.
Database Registry—Chemical Abstracts Service, Jul. 1, 2007—XP-002632609.
Database Registry—Chemical Abstracts Service, Oct. 6, 2003—XP-002632610.
Database Registry—Chemical Abstracts Service, May 23, 2003—XP-002632611.
Database Registry—Chemical Abstracts Service, Jul. 29, 2001—XP-002632612.
Database Registry—Chemical Abstracts Service, Feb. 19, 2001—XP-002632613.
Database CA [Online]—Chemical Abstracts Service, Jun. 28, 2000—XP-002632614.
Database CA [Online]—Chemical Abstracts Service, Jan. 1, 2001—XP-002632615.
Database Registry—Chemical Abstracts Service, Feb. 1, 2009—XP-002632616.
Database Registry—Chemical Abstracts Service, Feb. 1, 2009—XP-002632617.
Edmont D. et al.—"Synthesis and Evaluation of Quinoline Carboxyguanidines as Antidiabetic Agents"—Bioorganic & Medical Chemistry Letters 10, vol. 10, pp. 1831-1834, (2000).
Thorsten L. et al.,—"3,6-Bis(2-arylethenyl)-1,2,4,5-tetrazine—Synthese, Flussigkristallinitat and Photochemie"—Journal fur praktische Chemie Chemiker-Zeitung, vol. 337, pp. 641-646, (1995).

\* cited by examiner

GUANIDINE DERIVATIVES IN CINNAMIC SERIES

BACKGROUND

1. Field of the Invention

The present invention relates to novel guanidine derivatives in the cinnamic series, to a process for preparing them and to their use for the preparation of compositions with anti-glycation properties, especially in cosmetology.

2. Description of the Related Art

Aging of the skin is caused by three main factors: free radicals, UV radiation and the glycation process.

Glycation is a bonding reaction between a sugar and a protein, which leads to the formation of glycation products that can neither be destroyed nor evacuated from cells and whose accumulation causes aging of the cells.

Aminoguanidine is an agent that is known for its anti-glycation properties.

However, there is a constant need to provide agents with even better anti-glycation properties.

SUMMARY OF THE INVENTION

The Applicant has now designed novel guanidine derivatives in the cinnamic series, of novel structure, which gives them advantageous properties for combating aging of the skin, namely calmative properties, combined with antioxidant and anti-glycation properties, such properties making them active principles of choice in the cosmetological field.

DETAILED DESCRIPTION OF THE PREFERRED EMBODIMENTS

The novel derivatives according to the invention correspond more specifically to the general formula (I):

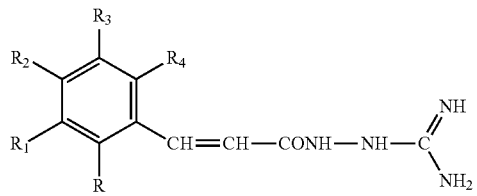
(I)

in which:

R represents a hydrogen atom or a C1-C4 alkoxy group,
R1 represents a hydrogen atom, a C1-C4 alkoxy group, a group NO2 or a group OH,
R2 represents a hydrogen atom, a C1-C4 alkoxy group or a group OH,
R1 and R2 may also together form a group OCH2O,
R3 represents a hydrogen atom or a C1-C4 alkoxy group, and
R4 represents a hydrogen atom,
and also salts thereof and isomers thereof.

According to one embodiment, the set (R, R1, R2, R3, R4) is chosen from the group consisting of (H, H, H, H, H), (H, NO2, H, H, H), (C1-C4 alkoxy, H, H, H, H) and (H, C1-C4 alkoxy, OH, H, H).

According to another embodiment, R1 and R2 together form a group OCH2O, and R, R3 and R4 each represent a hydrogen atom.

The present invention extends to all the isomers of the derivatives of formula (I) and to the salts thereof.

In particular, the present invention extends to the addition salts of a mineral acid such as HCl, HBr and H2SO4, and also to the addition salts of an organic acid such as methanesulfonic acid, benzoic acid, salicylic acid, lactic acid, citric acid, D or L malic acid, D glucuronic acid and hyaluronic acid.

The novel derivatives, isomers and salts according to the invention may be prepared via a process which comprises:

(i) the reaction of 3,5-dimethylpyrazole-1-carboxamidine nitrate with a compound of general formula (III) below:

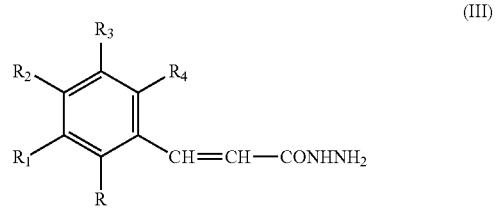
(III)

in which R, R1, R2, R3 and R4 have the same meaning as in formula (I),
to obtain the nitrate of a compound of formula (I),
(ii) the optional basification of the nitrate obtained in step (i), to obtain the compound of formula (I), and
(iii) the optional salification of the compound of formula (I) obtained in step (ii) with a suitable mineral or organic acid.

The compound of formula (III) involved in step (i) of the process may be obtained via various routes.

According to one embodiment, the compound of formula (III) is prepared by reacting hydrazine with a compound of general formula (II) below (process A):

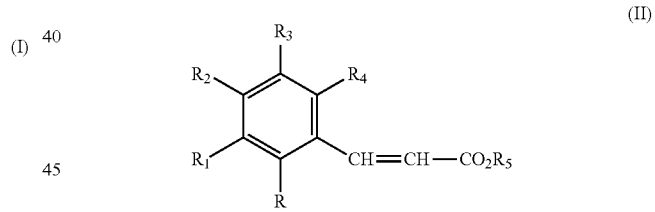
(II)

in which R, R1, R2, R3 and R4 have the same meaning as in formula (I) and R5 represents a C1-C4 alkyl group.

Alternatively, compound (III) is prepared according to the following steps (process B):

(iv) the reaction of 1-(methylsulfonyl)benzotriazole with a compound of general formula (IV) below:

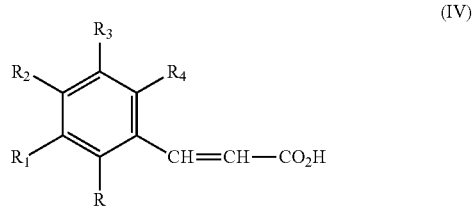
(IV)

in which R, R1, R2, R3 and R4 have the same meaning as in formula (I), to obtain a compound of general formula (V) below:

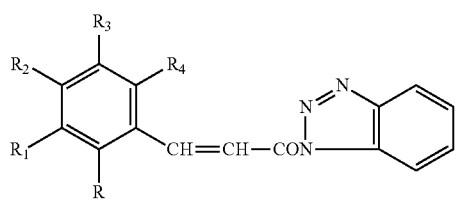

in which R, R1, R2, R3 and R4 have the same meaning as in formula (I), and (v) the reaction of the compound of formula (V) obtained in step (iv) with hydrazine to obtain the compound of formula (III).

When a compound of formula (IV) comprising a group —OH is used, it is preferable to protect this function by substituting this group with, for example, a group —OCH3, before performing step (iv).

The invention also concerns the novel synthetic intermediates of general formula (III) below:

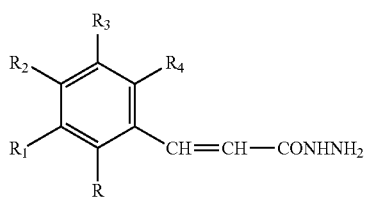

in which R, R1, R2, R3 and R4 have the same meaning as in formula (I).

According to a preferred embodiment, the synthetic intermediates of formula (III) are such that the set (R, R1, R2, R3, R4) is chosen from the group consisting of (H, H, H, H, H), (H, NO2, H, H, H), (C1-C4 alkoxy, H, H, H, H) and (H, C1-C4 alkoxy, OH, H, H).

The invention also relates to the synthetic intermediates of general formula (V) below:

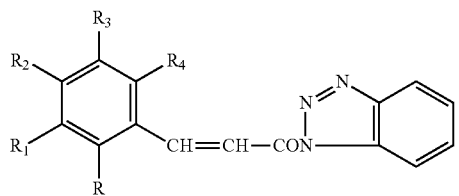

in which R, R1, R2, R3 and R4 have the same meaning as in formula (I).

According to a preferred embodiment, the synthetic intermediates of formula (V) are such that the set (R, R1, R2, R3, R4) is chosen from the group consisting of (H, H, H, H, H), (H, NO2, H, H, H), (C1-C4 alkoxy, H, H, H, H) and (H, C1-C4 alkoxy, OH, H, H).

The invention also extends to the use of the derivatives of formula (I), salts thereof and isomers thereof, for the preparation of an anti-glycation composition, in particular in a cosmetic composition.

Finally, the invention relates to a cosmetic composition comprising at least one derivative of formula (I), an isomer or salt thereof and a cosmetically acceptable vehicle.

The preparation of a certain number of derivatives of formula (I), of synthetic intermediates of formula (III) and of synthetic intermediates of formula (V), collated respectively in Tables 1, 2 and 3, will now be described in greater detail.

TABLE 1

Compounds of formula (I)

| | R | R1 | R2 | R3 | R4 |
|---|---|---|---|---|---|
| 29 | H | OCH3 | OH | H | H |
| 30 | H | OCH3 | OH | H | H |
| 31 | H | OCH3 | OH | H | H |
| 32 | H | OCH3 | OH | H | H |
| 33 | H | OCH3 | OH | H | H |
| 34 | H | OCH3 | OH | H | H |
| 35 | H | OCH3 | OH | H | H |
| 36 | H | OCH3 | OH | H | H |
| 37 | H | H | H | H | H |
| 38 | H | R1 + R2 form a group OCH2O | | H | H |
| 39 | H | NO2 | H | H | H |
| 40 | OCH3 | H | H | H | H |
| 41 | H | OCH3 | H | H | H |
| 42 | H | OH | H | H | H |
| 43 | OC2H5 | H | H | H | H |
| 44 | OCH3 | H | H | OCH3 | H |
| 45 | OC2H5 | H | H | H | H |
| 46 | OCH3 | H | H | OCH3 | H |
| 47 | OC2H5 | H | H | H | H |
| 48 | OCH3 | H | H | OCH3 | H |

TABLE 2

Compounds of formula (III)

| | R | R1 | R2 | R3 | R4 |
|---|---|---|---|---|---|
| 14 | H | H | H | H | H |
| 15 | H | R1 + R2 form a group OCH2O | | H | H |
| 16 | H | NO2 | H | H | H |
| 17 | OCH3 | H | H | H | H |
| 18 | H | OCH3 | H | H | H |
| 19 | H | OH | H | H | H |
| 21 | H | H | OCH3 | H | H |
| 22 | OC2H5 | H | H | H | H |
| 23 | H | OCH3 | OCH3 | H | H |
| 24 | H | OCH3 | H | OCH3 | H |
| 25 | H | OH | OCH3 | H | H |
| 26 | H | OCH3 | OH | H | H |
| 27 | H | OCH3 | OCH3 | OCH3 | H |
| 28 | OCH3 | OCH3 | OCH3 | H | H |

TABLE 3

Compounds of formula (V)

| | R | R1 | R2 | R3 | R4 |
|---|---|---|---|---|---|
| 1 | H | H | H | H | H |
| 2 | H | R1 + R2 form a group OCH2O | | H | H |
| 3 | H | NO2 | H | H | H |
| 4 | OCH3 | H | H | H | H |
| 5 | H | OCH3 | H | H | H |
| 6 | H | OCOCH3 | H | H | H |
| 7 | H | OCH3 | OCOCH3 | H | H |
| 8 | H | H | OCH3 | H | H |
| 9 | OC2H5 | H | H | H | H |

TABLE 3-continued

Compounds of formula (V)

|    | R    | R1     | R2   | R3   | R4 |
|----|------|--------|------|------|----|
| 10 | OCH3 | H      | H    | OCH3 | H  |
| 11 | H    | OCOOCH3| OCH3 | H    | H  |
| 12 | H    | OCH3   | OCH3 | OCH3 | H  |
| 13 | OCH3 | OCH3   | OCH3 | H    | H  |

A certain number of examples illustrating the synthesis of the synthetic intermediates and of the derivatives according to the invention will be given below; the numbers appearing in these examples correspond to the compounds respectively bearing the same numbers in Tables 1 to 3 above.

Preparation of the Synthetic Intermediates of Formula (V)

Example 1

(E)-1-(benzotriazol-1-yl)-3-phenyl-2-propen-1-one 1.42 g (0.01 mol) of trans-cinnamic acid (compound of formula IV) and 1.97 g (0.01 mol) of 1-(methylsulfonyl) benzotriazole are stirred at room temperature in 50 ml of tetrahydrofuran, followed by dropwise addition of 0.014 mol of triethylamine. The solution is then refluxed for 24 hours, and then evaporated under reduced pressure. The residue is taken up in 60 ml of water and extracted with 70 ml of ethyl acetate. The organic phase is dried, filtered and then concentrated under vacuum. The powder obtained is taken up in 50 ml of acetonitrile and filtered off by suction.

2.24 g of a white powder are obtained.
Melting point: 157° C.

Example 2

1-[(2E)-3-(1,3-benzodioxol-5-yl)prop-2-enoyl]-1H-1,2,3-benzotriazole

The procedure of Example 1 is used, starting with 1.92 g (0.01 mol) of 3,4-(methylenedioxy)cinnamic acid (compound of formula IV), 1.97 g (0.01 mol) of 1-(methylsulfonyl)benzotriazole and triethylamine.

1.80 g of a yellow powder are obtained.
Melting point: 198° C.
IR spectrum (KBr): 1693 (C=O)
NMR spectrum (CDCl3): 6.00 (s, 2H, CH2), 6.22 (d, J2-3: 15.60 Hz, 1H, H2), 6.81, 6.98 (m, 2H, H5', 6'), 7.48 (m, 5H, H-benzotriazole, H2'), 7.51 (d, J3-2: 15.60 Hz, 1H, H3)

Example 3

(E)-1-(benzotriazol-1-yl)-3-(3-nitrophenyl)-2-propen-1-one

The procedure of Example 1 is used, starting with 1.93 g of 3-nitrocinnamic acid (compound of formula IV), 1.97 g of 1-(methylsulfonyl)benzotriazole and 0.014 mol of triethylamine.

2.68 g of a white powder are obtained.
Melting point: 230° C.
IR spectrum (KBr): 1704 (C=O)
1H NMR spectrum (DMSO d6): 7.65 (d, d, J: 8.1, 7.5 Hz, 1H), 7.78 (dd, 2H), 8.25, 8.27, 8.31 (m, 6H), 8.68 (s, 1H, H2').

Example 4

(E)-1-(benzotriazol-1-yl)-3-(2-methoxyphenyl)-2-propen-1-one

The procedure of Example 1 is used, starting with 1.78 g (0.01 mol) of 2-methoxycinnamic acid (compound of formula IV), 1.97 g (0.01 mol) of 1-(methylsulfonyl)benzotriazole and 0.014 mol of triethylamine.

2.30 g of a white powder are obtained.
Melting point: 158° C.
IR spectrum (KBr): 1699 (C=O)
1H NMR spectrum (CDCl3): 3.97 (s, 3H, OCH3), 6.99, 7.02 (multiplet, 2H), 7.69, 7.75 (multiplet, 2H), 8.13, (d, J3'4': 8.75 Hz, 1H, H3'=, 8.21 (d, J2-3: 15.80 Hz, 1H, H2), 8.44 (d, J: 7.79 Hz, 1H, H benzotriazole), 8.51 (d, J3-2: 15.60 Hz, 1H, H3).

Example 5

(E)-1-(benzotriazol-1-yl)-3-(3-methoxyphenyl)-2-propen-1-one

The procedure of Example 1 is used, starting with 1.78 g (0.01 mol) of 3-methoxycinnamic acid (compound of formula IV), 1.97 g (0.01 mol) of 1-(methylsulfonyl)benzotriazole and 0.014 mol of triethylamine.

2.15 g of a white powder are obtained.
Melting point: 156° C.
IR spectrum (KBr): 1710 (C=O)
1H NMR spectrum (CDCl3): 3.90 (s, 3H, OCH3), 7.05 (d, 1H, H benzotriazole), 7.25 (d, 1H, H benzotriazole), 7.37 (m, 2H, H5', H benzotriazole), 7.53 (d, d, J5'-6', 5'-4': 7.90, 7.30 Hz, 1H, H5'), 8.11 (m, 2H, H2', H benzotriazole), 8.14 (d, J2-3: 16.1 Hz, 1H, H1), 8.42 (d, J3-2: 16.1 Hz, 1H, H3).

Example 6

(E)-1-(benzotriazol-1-yl)3-3(3-acetyloxyphenyl)-2-propen-1-one

The procedure of Example 1 is used, starting with 2.05 g (0.01 mol) of (2E)-3-(3-acetyloxyphenyl)acrylic acid (compound of formula IV), 1.97 g (0.01 mol) of 1-methylsulfonyl) benzotriazole and 0.014 mol of triethylamine.

2.1 g of a white powder are obtained.
Melting point: 156° C.
IR spectrum (KBr): 1750, 1690 (C=O)
1H NMR spectrum (DMSO d6): 2.26 (s, 3H, OCOCH3), 7.10 (d, 1H, H benzotriazole), 7.23 (d, 1H, H benzotriazole), 7.30 (m, 2H, H6', H benzotriazole), 7.50 (d, d, J5'-6': 7.85 Hz, J5'-4': 7.30 Hz, 1H, H5'), 8.02 (m, 2H, H benzotriazole), 8.10 (d, J2-3: 15.8 Hz 1H, H2), 8.36 (d, J3-2: 15.8 Hz, 1H, H3).

The compound of formula V of Example 6 may be prepared starting with 3-hydroxycinnamic acid (also a compound of formula IV), the hydroxyl function of which has been protected beforehand in the following manner.

5 g (0.030 mol) of 3-hydroxycinnamic acid are stirred in 50 ml of pyridine for 24 hours in the presence of 3 ml of acetic anhydride and 0.16 g (0.013 mol) of dimethylaminopyridine. The solution is concentrated under reduced pressure, and the residue is taken up in 150 ml of 10% hydrochloric acid solution and extracted with twice 120 ml of ethyl acetate.

(2E)-3-(3-Acetyloxyphenyl)acrylic acid is obtained, which may be used for the preparation of the compound of Example 6.

Example 7

(E)-1-(benzotriazol-1-yl)-3-(4-acetyloxy-3-methoxyphenyl)-2-propen-1-one

The procedure of Example 1 is used, starting with 2.36 g (0.01 mol) of 4-(acetyloxy)ferulic acid (compound of formula IV), 1.97 g (0.01 mol) of 1-(methylsulfonyl)benzotriazole and 0.014 mol of triethylamine.

3.01 g of a white powder are obtained.
Melting point: 160° C.
IR spectrum (KBr): 1752, 1690 (C=O)
1H NMR spectrum (DMSO d6): 2.27 (s, 3H, COCH3), 3.88 (s, 3H, OCH3), 7.22 (d, J: 7.83 Hz, 1H, H benzotriazole), 7.50 (d, J6'-5': 8.30 Hz, 1H, H6'), 7.2 (t, 1H, H benzotriazole), 7.70 (s, 1H, H2'), 7.79 (t, 1H, H benzotriazole), 8.10 (m, 2H, H2, H3), 8.27 (d, J: 7.38 Hz, 1H, H benzotriazole), 8.33 (d, J5'-6': 7.83 Hz, 1H, H5')

The compound of formula V may also be obtained from another compound of formula IV, namely ferulic acid, the hydroxyl function of which has been protected beforehand in the following manner.

At room temperature, 50 g (0.258 mol) of ferulic acid are dissolved in pyridine. 1.6 g (0.0131 mol) of DMAP are added to the reaction medium, followed by dropwise addition of 27 ml of acetic anhydride. After stirring for 18 hours at room temperature, the solution is poured into 1 liter of cold water and the precipitate formed is filtered off by suction, washed 3 times with 500 ml of water, dried and recrystallized from ethanol.

4-(Acetyloxy)ferulic acid is obtained, which may be used for the preparation of the compound of Example 7.

Example 8

(E)-1-(benzotriazol-1-yl)-3-(4-methoxyphenyl)-2-propen-1-one

The procedure of Example 1 is used, starting with 1.78 g (0.01 mol) of 4-methoxycinnamic acid (compound of formula IV), 1.97 g (0.01 mol) of 1-(methylsulfonyl)benzotriazole and 0.014 mol of triethylamine.

2.1 g of a white powder are obtained.
Melting point: 186° C.
IR spectrum (KBr): 1697 (C=O)
1H NMR spectrum (CDCl3): 3.88 (s, 3H, OCH3), 6.62 (d, J2-3: 16.50 Hz, 1H), 6.99 (d, 2H), 7.46 (m, 3H), 7.48 (d, 2H), 8.02 (d, J: 6.83 Hz, 1H), 8.09 (d, J: 7.83 Hz, 1H)

Example 9

(E)-1-(benzotriazol-1-yl)-3-(2-ethoxyphenyl)-2-propen-1-one

The procedure of Example 1 is used, starting with 1.92 g (0.01 mol) of 2-ethoxycinnamic acid (compound of formula IV), 1.97 g (0.01 mol) of 1-(methylsulfonyl)benzotriazole and 0.014 mol of triethylamine.

2 g of a white powder are obtained.
Melting point: 150° C.
IR spectrum (KBr): 1711 (C=O)
1H NMR spectrum (CDCl3): 1.57 (t, 3H, CH3), 4.19 (q, 2H, CH2), 6.97, 7.02 (multiplet, 2H), 7.41, 7.52 (multiplet, 2H), 7.67, 7.73 (multiplet, 2H), 8.13 (d, J3'-4': 8.79 Hz, 1H, 3H'), 8.25 (d, J2-3: 16.58 Hz, 1H, H2), 8.44 (d, J: 8.80 Hz, 1H, H benzotriazole), 8.50 (d, J3-2: 15.60 Hz, 1H, H3).

Example 10

(E)-1-(benzotriazol-1-yl)-3-(2,5-dimethoxyphenyl)-2-propen-1-one

The procedure of Example 1 is used, starting with 2.08 g (0.01 mol) of 2,5-dimethoxycinnamic acid (compound of formula IV), 1.97 g (0.01 mol) of 1-(methylsulfonyl)benzotriazole and 0.014 mol of triethylamine.

1.98 g of a white powder are obtained.
Melting point: 144° C.
IR spectrum (KBr): 1700 (C=O)
1H NMR spectrum (CDCl3): 3.85 (s, 3H, OCH3), 3.92 (s, 3H, OCH3), 6.92 (d, 1H, H benzotriazole), 7.03 (q, J6'-4': 2.91 Hz, 1H, H6'), 7.54, 7.66 (multiplet, 2H, H benzotriazole), 8.17 (q, J2-3: 15.60 Hz, J3'-4': 8.79 Hz, 2H, H2, H3'), 8.24 (d, J: 7.83 Hz, 1H, H benzotriazole), 8.50 (d, J3-2: 15.60 Hz, 1H, H3)

Example 11

(E)-1-(benzotriazol-1-yl)-3-(3-acetyloxy-4-methoxyphenyl)-2-propen-1-one

The procedure of Example 1 is used, starting with 2.36 g (0.01 mol) of (2E)-3-[(3-acetyloxy)-4-methoxyphenyl]acrylic acid (compound of formula IV), 1.97 g (0.01 mol) of 1-(methylsulfonyl)benzotriazole and 0.014 mol of triethylamine.

2.95 g of a white powder are obtained.
Melting point: 152° C.
IR spectrum (KBr): 1754, 1693 (C=O)
1H NMR spectrum (DMSO d6): 2.28 (s, 3H, COCH3), 3.92 (s, 3H, OCH3), 7.24 (d, J: 8.79 Hz, 1H, H benzotriazole), 7.60, 7.79 (m, 4H, H5', H benzotriazole), 7.94 (d, J2-3: 15.60 Hz, 1H, H2), 8.09 (d, J3-2: 15.62 Hz, 1H, H3), 8.26 (d, J5'-6': 7.79 Hz, 1H, H5'), 8.31 (d, J6'-5': 7.80 Hz, 1H, H6')

The compound of formula IV, (2E)-3-[(3-acetyloxy)-4-methoxyphenyl]acrylic acid, may be obtained from another compound of formula IV, namely 3-hydroxy-4-methoxycinnamic acid, in the following manner.

15 g (0.077 mol) of 3-hydroxy-4-methoxycinnamic acid are stirred in 50 ml of pyridine for 24 hours, in the presence of 8.1 ml of acetic anhydride and 0.48 g (0.0039 mol) of dimethylaminopyridine. The solution is concentrated under reduced pressure, and the residue is taken up in 150 ml of 10% hydrochloric acid solution and extracted with twice 120 ml of ethyl acetate.

Example 12

(E)-1-(benzotriazol-1-yl)-3-(3,4,5-trimethoxyphenyl)-2-propen-1-one

The procedure of Example 1 is used, starting with 2.38 g (0.01 mol) of 3,4,5-trimethoxycinnamic acid (compound of formula IV), 1.97 g (0.01 mol) of 1-(methylsulfonyl)benzotriazole and 0.014 mol of triethylamine.

3 g of a yellow powder are obtained.
Melting point: 136° C.

Example 13

(E)-1-(benzotriazol-1-yl)-3-(2,3,4-trimethoxyphenyl)-2-propen-1-one

The procedure of Example 1 is used, starting with 1.97 g (0.01 mol) of 2,3,4-trimethoxycinnamic acid (compound of formula IV), 1.97 g (0.01 mol) of 1-(methylsulfonyl)benzotriazole and 0.014 mol of triethylamine.

3.1 g of a white powder are obtained.
Melting point: 138° C.
IR spectrum (KBr): 1706 (C=O)
1H NMR spectrum (DMSO d6): 3.78 (s, 3H, OCH3), 3.87 (s, 3H, OCH3), 3.91 (s, 3H, OCH3), 6.95 (d, J: 8.75 Hz, 1H, H benzotriazole), 7.15 (m, 3H, H benzotriazole), 8.02 (d, J3-2: 16.58 Hz, 1H, H2), 8.20 (d, J3-2: 16.6 Hz, 1H, H3), 8.32 (d, J5'-6': 7.83 Hz, 1H, H5')

Preparation of the Synthetic Intermediates of Formula (III)

Example 14

(2E)-3-phenylacrylohydrazide

Process A 5 g (0.031 mol) of methyl cinnamate (compound of formula II) in 50 ml of hydrazine hydrate are stirred at 70° C. for 1 hour 30 minutes.

After cooling, the solution is concentrated under vacuum and the residue is stirred for one hour in 60 ml of cold water. The precipitate is filtered off by suction, washed with acetonitrile and then with ether, and dried.

0.30 g of a white powder is obtained.
Melting point: 116° C.
IR spectrum (KBr): 3234 (NH), 1650 (C=O)
1H NMR spectrum (DMSO): 3.60 (s, 2H, NH2), 6.38 (d, J2.3: 15.7 Hz, 1H, H2), 7.00 (s, 1H, NH), 7.38, 7.52 (m, 5H, H phenyl), 7.71 (d, J3.2: 15.7 Hz, 1H, H3)

Process B 3 g (0.0120 mol) of the derivative (E)-1-(benzotriazol-1-yl-3-phenyl-2-propen-1-one) (compound of formula V, obtained in Example 1) are stirred at room temperature in 40 ml of tetrahydrofuran in the presence of 0.66 g (0.0132 mol) of hydrazine hydrate. After stirring for 3 hours, the solution is concentrated under reduced pressure and the residue is taken up in 50 ml of potassium carbonate solution and extracted with 100 ml of ethyl acetate. The organic phase is dried over magnesium sulfate and then concentrated under vacuum.

1.65 g of a white powder are obtained.
Melting point: 116° C.
The IR and 1H NMR spectra are identical to those obtained according to process A.

Example 15

(2E)-(3,4-methylenedioxy)acrylohydrazide

The same procedure as that of process B of Example 14 is used, starting with 2.93 g (0.01 mol) of N-acylbenzotriazole (compound of formula V) obtained in Example 2 and 0.6 g (0.012 mol) of hydrazine hydrate.

1.3 g of a white powder are obtained.
Melting point: 136° C.
IR spectrum (KBr): 3264 (NH—NH2), 1656 (C=O)
1H NMR spectrum (CDCl3): 4.19 (s, 2H, NH2), 6.00 (s, 2H, OCH2O), 6.22 (d, J2-3: 15.60 Hz, 1H, H2), 6.81 (d, J5'-6': 7.73 Hz, 1H, H5'), 7.05 (m, 2H, H2', H6'), 7.14 (s, 1H, NH), 7.61 (d, J3-2: 15.65 Hz, 1H, H3).

Example 16

(2E)-3-(3-nitrophenyl)acrylohydrazide

The same procedure as that of process B of Example 14 is used, starting with 2.94 g (0.01 mol) of N-acylbenzotriazole (compound of formula V) obtained in Example 3, and 0.6 g (0.012 mol) of hydrazine hydrate.

1.80 g of a white powder are obtained.
Melting point: 196° C.
IR spectrum (KBr): 3332, 3237 (NH—NH2), 1610 (C=O)
1H NMR spectrum (DMSO d6): 4.51 (s, 2H, NH2), 6.74 (d, J2-3: 15.58 Hz, 1H, H3), 7.71 (t, 1H, H5'), 8.10 (d, J6'-5': 7.79 Hz, 1H, H6'), 8.20 (d, J4'-5': 7.80 Hz, 1H, H4'), 8.37 (s, 1H, H2'), 9.42 (s, 1H, NH).

Example 17

(2E)-3-(2-methoxyphenyl)acrylohydrazide

The same procedure as that of process B of Example 14 is used, starting with 2.79 g (0.01 mol) of N-acylbenzotriazole (compound of formula V) obtained in Example 4, and 0.6 g (0.012 mol) of hydrazine hydrate.

1.45 g of a white powder are obtained.
Melting point: 120° C.
IR spectrum (KBr): 3306, 3300 (NH—NH2), 1603 (C=O)
1H NMR spectrum (CDCl3): 3.85 (s, 3H, OCH3), 4.11 (s, 2H, NH2), 6.54 (s, 2H, (d, J2-3: 15.60 Hz, 1H, H2), 6.88 (multiplet, 2H, H5'-6'), 7.31 (d, d, 1H', H4'), 7.44 (d, J3'-4': 8.79 Hz, 1H, H3'), 7.50 (s, 1H, NH), 7.95 (d, J3-2: 15.58 Hz, 1H, H3).

Example 18

(2E)-3-(3-methoxyphenyl)acrylohydrazide

The same procedure as that of process B of Example 14 is used, starting with 2.79 g (0.01 mol) of N-acylbenzotriazole (compound of formula V) obtained in Example 5, and 0.6 g (0.012 mol) of hydrazine hydrate.

1.5 g of a white powder are obtained.
Melting point: 130° C.
IR spectrum (KBr): 3324, 3240 (NH—NH2), 1603 (C=O)
1H NMR spectrum (CDCl3): 3.82 (s, 3H, OCH3), 4.01 (s, 2H, NH2), 6.38 (s, 2H, (d, J2-3: 15.58 Hz, 1H, H2), 6.92 (d, J6'-5': 6.79 Hz, 1H, H6'), 7.02 (d, J2'-6': 1.91 Hz, 1H, H2'), 7.11 (d, J4'-5': 7.79 Hz, 1H, H4'), 7.14 (s, 1H, NH), 7.30 (m, 1H, H5'), 7.67 (d, J3-2: 15.60 Hz, 1H, H3).

Example 19

(2E)-3-(3-hydroxyphenyl)acrylohydrazide

The same procedure as that of process B of Example 14 is used, starting with 3.07 g (0.01 mol) of N-acylbenzotriazole (compound of formula V) obtained in Example 6, and 0.6 g (0.012 mol) of hydrazine hydrate.

0.7 g of a white powder is obtained.
Melting point: 132° C.
IR spectrum (KBr): 3400, 3290, 3200 (OH, NH—NH2), 1682 (C=O)
1H NMR spectrum (DMSO d6): 4.07 (s, 2H, NH2), 6.58 (d, J2-3: 15.56 Hz, 1H, H2), 6.79 (d, 1H, H4'), 6.85 (s, 1H, H2'), 6.96 (d, 1H, H6'), 7.19 (q, 1H, H5'), 7.43 (d, J3-2: 15.60 Hz, 1H, H3), 8.50 (s, 1H, NH), 9.75 (s, 1H, OH).

Example 21

(2E)-3-(4-methoxyphenyl)acrylohydrazide

The same procedure as that of process B of Example 14 is used, starting with 2.79 g (0.01 mol) of N-acylbenzotriazole (compound of formula V) of Example 8, and 0.6 g (0.012 mol) of hydrazine hydrate.

1.75 g of a white powder are obtained.
Melting point: 140° C.
IR spectrum (KBr): 3311, 3279 (NH NH2), 1655 (C=O)
1H NMR spectrum (DMSO d6): 3.76 (s, 3H, OCH3), 4.40 (s, 2H, NH2), 6.40 (d, J2-3: 15.60 Hz, 1H, H2), 6.96 (d, 2H, H2'6'), 7.39 (d, J3-2: 15.58 Hz, 1H, H3), 7.49 (d, 2H, H3'5'), 9.23 (s, 1H, NH)

Example 22

(2E)-3-(2-ethoxyphenyl)acrylohydrazide

The same procedure as that of process B of Example 14 is used, starting with 2.93 g (0.01 mol) of N-acylbenzotriazole (compound of formula V) of Example 9, and 0.6 g (0.012 mol) of hydrazine hydrate.
1.35 g of a pale yellow oil are obtained.
IR spectrum (KBr): 3248, 3074 (NH NH2), 1655 (C=O)
1H NMR spectrum (CDCl3): 1.24 (t, 3H, CH2-CH3), 4.08 (q, 2H, CH2-CH3), 4.15 (s, 2H, NH2), 6.60 (d, J2-3: 16.58 Hz, 1H, H2), 6.90 (multiplet, 2H, H5'6'), 7.29 (dd, 1H, H4'), 7.43 (d, J3'-4': 8.70 Hz, 1H, H3'), 7.50 (s, 1H, NH), 8.01 (d, J3-2: 16.60 Hz, 1H, H3)

Example 23

(2E)-3-[3,4-dimethoxyphenyl]acrylohydrazide

Process A is followed: 5 g (0.0225 mol) of methyl 3,4-dimethoxycinnamate (compound of formula II) in 45 ml of hydrazine hydrate are stirred at 70° C. for 1 hour 30 minutes. After cooling, the solution is concentrated under vacuum and the residue formed is stirred for one hour in 60 ml of water. The precipitate is filtered off by suction, washed with 20 ml of acetonitrile and dried.
2.65 g of a white powder are obtained.
Melting point: 196° C.
IR spectrum (KBr): 3322, 3232 (NH), 1651 (C=O)
1H NMR spectrum (DMSO d6): 3.77 (s, 6H, (OCH3)2), 4.38 (s, 2H, NH2), 6.43 (d, J2-3: 15.58 Hz, 1H, H2), 6.97 (d, J5'-6': 7.8 Hz, 1H, H5'), 7.08 (d, J6'-5': 7.8 Hz, 1H, H6'), 7.12 (s, 1H, H2'), 7.38 (d, J3-2: 15.60 Hz, 1H, H3), 9.20 (s, 1H, NH)

Example 24

(2E)-3-(2,5-dimethoxyphenyl)acrylohydrazide

The same procedure as that of process B of Example 14 is used, starting with 3.09 g (0.01 mol) of N-acylbenzotriazole (compound of formula V) of Example 10, and 0.6 g (0.012 mol) of hydrazine hydrate.
1.35 g of a pale yellow powder are obtained.
Melting point: 136° C.
IR spectrum (KBr): 3299, 3204 (NH NH2), 1686 (C=O)
1H NMR spectrum (CDCl3): 3.76 (s, 3H, OCH3), 3.81 (s, 3H, OCH3), 4.10 (s, 2H, NH2), 6.51 (d, J2-3: 15.58 Hz, 1H, H3), 6.88 (multiplet, 2H, H4'3'), 7.00 (s, 1H, H6'), 7.29 (s, 1H, NH), 7.91 (d, J3-2: 15.58 Hz, 1H, H3)

Example 25

(2E)-3-(3-hydroxy-4-methoxyphenyl)acrylohydrazide

The same procedure as that of process B of Example 14 is used, starting with 3.37 g (0.01 mol) of N-acylbenzotriazole (compound of formula V) of Example 11, and 0.6 g (0.012 mol) of hydrazine hydrate.

1.3 g of a cream-colored powder are obtained.
Melting point: 184° C.
IR spectrum (KBr): 3340, 3335 (OH, NH NH2), 1652 (C=O)
1H NMR spectrum (DMSO d6): 3.77 (s, 3H, OCH3), 4.20 (s, 2H, NH2), 6.25 (d, J2-3: 15.2 Hz, 1H, H2), 6.92 (m, 3H, H2', H5, H'6'), 7.29 (d, J3-2: 15.6 Hz, 1H, H3), 9.21, 9.18 (m, 2H, OH, NH)

Example 26

(2E)-3-(3-hydroxy-4-methoxyphenyl)acrylohydrazide

According to process A, 5 g (0.024 mol) of methyl ferulate (compound of formula II) in 50 ml of hydrazine hydrate are stirred at 70° C. for 1 hour 30 minutes. After cooling, the solution is concentrated under reduced pressure and the residue formed is stirred for one hour in 60 ml of water. The precipitate is filtered off by suction, washed with 20 ml of acetonitrile and dried.
A white powder is obtained.
Melting point: 158° C.
IR spectrum (KBr): 3415, 3308, 3244 (NH, OH), 1659 (C=O)
1H NMR spectrum (DMSO d6): 3.85 (s, 3H, OCH3), 4.15 (s, 2H, NH2), 6.13 (d, J2-3: 15.74 Hz, 1H, H2), 6.85 (d, J5'-6': 7.99 Hz, 1H, H5'), 7.05 (d, J6'-5': 7.99 Hz, 1H, H6'), 7.16 (s, 1H, H2'), 7.42 (d, J3-2: 15.72 Hz, 1H, H3), 9.23 (s, 1H, NH)
The compound of Example 26 may also be prepared according to process A, by following the same procedure as indicated above, but starting with ethyl ferulate.
A pinkish powder is obtained.
Melting point: 158° C.
The IR and NMR spectra are identical to those obtained for the compound of Example 6 prepared according to process A.
Finally, the compound of Example 26 may be obtained according to process B, by following the same procedure as that of process B of Example 14, starting with 3.37 g (0.01 mol) of the benzotriazole derivative (compound of formula V) of Example 7, and 0.6 g (0.012 mol) of hydrazine hydrate.

Example 27

(2E)-3-(3,4,5-trimethoxyphenyl)acrylohydrazide

The same procedure as that of process B of Example 14 is used, starting with the N-acylbenzotriazole (compound of formula V) of Example 12, and hydrazine hydrate.
2.10 g of a yellow powder are obtained.
Melting point: 154° C.

Example 28

(2E)-3-(2,3,4-trimethoxyphenyl)acrylohydrazide

The same procedure as that of process B of Example 14 is used, starting with 3.39 g (0.01 mol) of the N-acylbenzotriazole (compound of formula V) of Example 13, and 0.6 g (0.012 mol) of hydrazine hydrate.
2.05 g of a white powder are obtained.
Melting point: 148° C.
IR spectrum (KBr): 3319, 3266 (NH NH2), 1650 (C=O)
1H NMR spectrum (CDCl3): 3.88 (s, 8H, OCH3), 4.09 (s, 2H, NH2), 6.43 (d, J2-3: 15.58 Hz, 1H, H2), 6.38 (d, J6'-5': 8.79 Hz, 1H, H6'), 7.11 (s, 1H, NH), 7.22 (d, J5'-6': 8.80 Hz, 1H, H5'), 7.83 (d, J3-2: 15.62 Hz, 1H, H3)

Preparation of the guanidine derivatives of formula (I) and salts thereof.

Example 29 imino{2-[(2E)-3-(4-hydroxy-3-methoxyphenyl)prop-2-enoyl]hydrazino}methanaminium nitrate, (FAG Nitrate)

5 g (0.024 mol) of the hydrazide derivative of Example 26 in 45 ml of acetonitrile are refluxed for 2 hours 30 minutes in the presence of 4.83 g (0.024 mol) of 3,5-dimethylpyrazole-1-carboxamidine nitrate. After cooling, the solution is concentrated under vacuum and the residue is taken up in 50 ml of ethyl ether, stirred and filtered through a sinter.

6.35 g of a white powder are obtained.
Melting point: 224° C.
IR spectrum (KBr): 3394, 3343, 3281, 3155, 3020 (NH, NH3+, OH), 1694 (C=O)
1H NMR spectrum (DMSO d6): 3.79 (s, 3H, OCH3), 6.42 (d, J2-3: 15.62 Hz, 1H, H2), 6.82 (d, J5'-6': 8.70 Hz, 1H, H5'), 7.06 (d, J6'-5': 8.70 Hz, 1H, H6'), 7.15 (s, 1H, H2'), 7.40 (s, 3H, NH3+), 7.50 (d, J3-2: 15.60 Hz, 1H, H3), 9.47, 9.60 (s, 2H, NH), 10.87 (s, H, OH)

Example 30

{2[(2E)-3-(4-hydroxy-3-methoxyphenyl)prop-2-enyl]hydrazino}(imino)methaneamino (FAG)

3 g (0.00958 mol) of the compound of Example 29 are dissolved at 80° C. in 50 ml of water.

After cooling, the solution is basified with saturated potassium hydrogen carbonate solution. The precipitate is filtered off by suction, washed with water and dried.

2 g of a yellow powder are obtained.
Melting point: 198° C.
IR spectrum (KBr): 3543, 3395, 3390, 3244 (OH, NH), 1700 (C=O)
1H NMR spectrum (DMSO d6): 3.77 (s, 3H, OCH3), 6.38 (d, J3-2: 15.74 Hz, 1H, H3), 6.76 (d, 1H, H5'), 6.92 (m, 3H, H6', NH), 6.91 (m, 3H, H6', NH), 7.14 (m, 6H, H2, OH, NH)
1H NMR spectrum (D2O): 3.73 (s, 3H, OCH3), 6.38 (d, 1H, H2), 6.75 (d, 1H, H5'), 6.96 (d, 1H, H6'), 7.06 (s, 1H, H2'), 7.22 (d, J2-3: 15.60 Hz, 1H, H3)

Example 31 imino{2-[(2E)-3-(4-hydroxy-3-methoxyphenyl)prop-2-enoyl]hydrazino}methanaminium hydrochloride 0.5 g (0.002 mol) of the derivative of Example 30 is stirred at 50° C. in 25 ml of absolute ethanol, followed by dropwise addition of 0.25 ml of concentrated hydrochloric acid, and the mixture is then left at this temperature for 2 hours. After cooling, the precipitate is filtered off by suction, washed with 5 ml of acetonitrile and 5 ml of ethyl ether and dried.

0.48 g of a white powder is obtained.

Example 32 imino{2-[(2E)-3-(4-hydroxy-3-methoxyphenyl)prop-2-enoyl]hydrazino}methanaminium hydrobromide The protocol of Example 29 is followed, but reacting 0.5 g (0.002 mol) of the compound of Example 30 with 0.20 ml of hydrobromic acid as a 33% solution in acetic acid.

0.5 g of a cream-colored powder is obtained.
Melting point: 186° C.

Example 33 amino{2-[(2E)-3-(4-hydroxy-3-methoxyphenyl)prop-2-enoyl]hydrazino}methanaminium sulfate The general protocol of Example 29 is followed, starting with 0.5 g (0.002 mol) of the compound of Example 30 and 0.25 ml of sulfuric acid.

0.58 g of a pale yellow powder is obtained.
Melting point: 228° C.

Example 34 imino{2-[(2E)-3-(4-hydroxy-3-methoxyphenyl)prop-2-enoyl]hydrazino}methanaminium methanesulfonate The general protocol of Example 29 is followed, starting with 0.5 g (0.002 mol) of the compound of Example 30 and 0.192 g (0.002 mol) of methanesulfonic acid.

0.51 g of a white powder is obtained.
Melting point: 190° C.

Example 35 imino{2-[(2E)-3-(4-hydroxy-3-methoxyphenyl)prop-2-enoyl]hydrazino}methanaminium benzoate The general protocol of Example 29 is followed, starting with 0.5 g (0.002 mol) of the compound of Example 30 and 0.244 g (0.002 mol) of benzoic acid.

0.60 g of a white powder is obtained.
Melting point: 204° C.

Example 36 imino{2-[(2E)-3-(4-hydroxy-3-methoxyphenyl)prop-2-enoyl]hydrazino}methanaminium glucuronate 0.0776 g (0.004 mol) of D-glucuronic acid is dissolved in 13 ml of water with stirring and 25 ml of ethyl alcohol are added. After stirring for 10 minutes, 1 g (0.004 mol) of the compound of Example 30 is added and the solution is heated at 60° C. for 2 hours 30 minutes. After cooling, the mixture is concentrated under reduced pressure and the residue is taken up in 20 ml of acetonitrile. After stirring for one hour, the precipitate obtained is filtered off by suction, washed with 15 ml of ethyl ether and dried.

0.9 g of a white powder is obtained.
Melting point: 190° C.
IR spectrum (KBr): 3342, 3300, 3100, 2970 (NH, OH, NH3+), 1674 (C=O)
1H NMR spectrum (DMSO d6): 3.12 (m, 2H, H glucuronic acid), 3.41 (m, 2H, H glucuronic acid), 3, 78 (s, 3H, OCH3), 4.31 (d, 1H, H glucuronic acid), 4.89 (m, 1H, OH), 6.44 (d, J2-3: 15.62 Hz, 1H, H2), 6.81 (d, J5'-6': 7.79 Hz, 1H, H5')

7.03 (d, J6'-5': 7.80, 1H, H6'), 7.45 (s, 1H, H2'), 7.47 (d, J3-2: 15.62 Hz, 1H, H3), 8.04, 10.50 (m, OH, NH, NH3+)

Example 37 imino{2-[(2E)-3-(phenyl)prop-2-enoyl]hydrazine}methanaminium nitrate

The synthetic procedure of Example 29 is followed, starting with 1.62 g (0.01 mol) of the compound of formula III of Example 14 and 2.01 g (0.01 mol) of 3,5-dimethylpyrazole-1-carboxamidine nitrate.

1.30 g of a white powder are obtained.

IR spectrum (KBr): 3437, 32825, 3176, 3065, 3026 (NH—NH, C NH NH3+), 1693 (C=O)

1H NMR spectrum (DMSO d6): 6.62 (d, J2-3: 15.62 Hz, 1H, H2), 7.60, 7.44 (m, 9H, C6H5, CH3, NH), 10.00 (s, 3H, NH3+)

Example 38 imino{2-[(2E)-3-(1,3-benzodioxol-5-yl)prop-2-enoyl]hydrazine}methanaminium nitrate The synthetic procedure of Example 29 is followed, starting with 2.06 g (0.01 mol) of the compound of formula III of Example 15 and 2.01 g (0.01 mol) of 3,5-dimethylpyrazole-1-carboxamidine nitrate.

2.30 g of a white powder are obtained.

Melting point: 214° C.

IR spectrum (KBr): 3350, 3186, 2928, 2850 (NH—NH, C NH NH3+), 1666 (C=O)

1H NMR spectrum (DMSO d6): 6.07 (s, 2H, OCH2O), 6.44 (d, J2-3: 15.58 Hz, H, H2), 6.98 (d, J6'-5': 8.7 Hz, 1H, H6'), 7.14 (d, J6'-5': 8.70 Hz, 1H, H5'), 7.19 (s, 1H, H2'), 7.47 (m, 3H, NH3+), 9.46, 10.14 (m, 3H, NH)

Example 39 imino{2-[(2E)-3-(nitrophenyl)prop-2-enoyl]hydrazine}methanaminium nitrate

The synthetic procedure of Example 29 is followed, starting with 2.07 g (0.01 mol) of the compound of formula III of Example 16 and 2.01 g (0.01 mol) of 3,5-dimethylpyrazole-1-carboxamidine nitrate.

2 g of a white powder are obtained.

Melting point: 210° C.

IR spectrum (KBr): 3345, 3306, 3177, 3027 (NH—NH, C NH NH3+), 1696 (C=O)

1H NMR spectrum (DMSO d6): 6, 78 (d, J2-3: 15.58 Hz, 1H, H2), 7.58 (m, 3H, NH3+), 7.72 (m, 2H, H5', C H3), 8.13 (d, J6'-5': 8.7 Hz, 1H, H6'), 8.18 (d, J4'-5': 8.85 Hz, 1H, H4'), 8.44 (s, 1H, H2'), 9.46, 10.00 (m, 2H, NH)

Example 40 imino{2-[(2E)-3-(methoxyphenyl)prop-2-enoyl]hydrazine}methanaminium nitrate

The synthetic procedure of Example 29 is followed, starting with 1.92 g (0.01 mol) of the compound of formula III of Example 17 and 2.01 g (0.01 mol) of 3,5-dimethylpyrazole-1-carboxamidine nitrate.

1.40 g of a white powder are obtained.

Melting point: 180° C.

IR spectrum (KBr): 3437, 3308, 3174, 3021, 2959 (NH—NH, C NH NH3+), 1690 (C=O)

1H NMR spectrum (DMSO d6): 3.86 (s, 3H, OCH3), 6, 68 (d, J2-3: 15.58 Hz, 1H, H2), 7.02 (m, J5'-4': 7.79 Hz, J5'-6': 6.83 Hz, 1H, H5'), 7.11 (d, J6'-5': 7.79 Hz, 1H, H6'), 7.42 (d, J4'-3': 8.79 Hz, J4'-5': 7.79 Hz, 1H, H4'), 7.55 (d, J3'-4': 15.58 Hz, 1H, H3) 7.50 (m, 3H, NH3+), 7.78 (d, J3-2: 15.58 Hz, 1H, H3), 10.04 (m, 2H, NH)

Example 41 imino{2-[(2E)-3-(3-methoxyphenyl)-2-prop-2-enoyl]hydrazino}methanaminium nitrate The synthetic procedure for the derivative of Example 29 is followed, starting with 1.92 g (0.01 mol) of the compound of formula III of Example 18 and 2.01 g (0.01 mol) of 3,5-dimethylpyrazole-1-carboxamidine nitrate.

1.8 g of a white powder are obtained.

Melting point: 182° C.

IR spectrum (KBr): 3431, 3291, 3173, 3018 (NH NH C NH NH3+) 1693 (C=O)

1H NMR spectrum (DMSO d6): 3.77 (s, 3H, OCH3), 6.61 (d, J2-3: 16.58 Hz, 1H, H2), 6.99 (q, J6'-5': 5.83 Hz, J6'-2': 2.91 Hz, 1H, H6'), 7.15 (d, J2'-6': 2.91 Hz, 1H,H2'), 7.19 (d, J4'-5': 7.83 Hz, 1H, H4'), 7.35 (dd, 1H, H5'), 7.56 (d, J3-2: 18.58 Hz, 1H, H3), 7.60 (m, 3H, NH3+), 10.01 (m, 3H, NH)

Example 42 imino{2-[(2E)-3-(3-hydroxyphenyl)-2-prop-2-enoyl]hydrazino}methanaminium nitrate The synthetic procedure for the derivative of Example 29 is followed, starting with 1.78 g (0.01 mol) of the compound of formula III of Example 19 and 2.01 g (0.01 mol) of 3,5-dimethylpyrazole-1-carboxamidine nitrate.

0.8 g of a white powder is obtained.

Melting point: 178° C.

IR spectrum (KBr): 3420, 3290, 3180, 3020 (OH, NH NH C NH NH3+) 1690 (C=O)

1H NMR spectrum (DMSO d6): 6.34 (d, J2-3: 15.58 Hz, 1H, H2), 6.64 (m, 2H, H2', H4'), 6.99 (q, J6'-5': 6.10 Hz, H2, 1H, H6'), 7.30 (d, J5'-4': 7.80 Hz, J5'-6': 6.15 Hz, 1H, H5'), 7.40 (m, 3H, NH3+), 7.47 (d, J3-2: 15.58 Hz, 1H, H3), 8.40 (m, 3H, NH), 9.71 (s, 1H, OH)

Example 43 imino{2-[(2E)-3-(2-ethoxyphenyl)-2-prop-2-enoyl]hydrazino}methanaminium nitrate

The synthetic procedure for the derivative of Example 29 is followed, starting with 2.06 g (0.01 mol) of the compound of formula III of Example 22 and 2.01 g (0.01 mol) of 3,5-dimethylpyrazole-1-carboxamidine nitrate.

1.6 g of a white powder are obtained.

Melting point: 184° C.

IR spectrum (KBr): 3437, 3316, 3171, 2989 (NH NH C NH NH3+) 1691 (C=O)

1H NMR spectrum (DMSO d6): 1.39 (t, 3H, CH2CH3), 4.11 (q, 2H, CH2CH3), 6.68 (d, J2-3: 16.54 Hz, 1H, H2), 6.99 (dd, J5'-6': 8.79 Hz, J5'-4': 6.79 Hz, 1H, H5'), 7.09 (d, J6'-5': 8.79 Hz, 1H, H6'), 7.37 (d, d, J4'-5': 6.79 Hz, J4'-3': 8.79 Hz, 1H, H4'), 7.54 (d, J3'-4': 8.79 Hz, 1H, H3'), 7.60 (m, 3H, NH3+), 9.76, 10.20 (m, 3H, NH)

Example 44 imino{2-[(2E)-3-(2,5-dimethoxyphenyl)-2-prop-2-enoyl]hydrazino}methanaminium nitrate The synthetic procedure for the derivative of Example 29 is followed, starting with 2.22 g (0.01 mol) of the compound of formula III of Example 24 and 2.01 g (0.01 mol) of 3,5-dimethylpyrazole-1-carboxamidine nitrate.

2 g of a white powder are obtained.
Melting point: 208° C.
IR spectrum (KBr): 3402, 3380, 3184, 2960 (NH NH C NH NH3+) 1663 (C=O)
1H NMR spectrum (DMSO d6): 3.73 (s, 3H, OCH3), 3.81 (s, 3H, OCH3), 6.69 (d, J2-3: 15.58 Hz, 1H, H2), 6.99 (d, d, J4'-3': 8.75 Hz, J4'-6': 2.91 Hz, 1H, H4'), 7.05 (d, J3'-4': 8.75 Hz, 1H, H3'), 7.08 (d, J6'-4': 2.91 Hz, 1H, H6'), 7.35 (m, 3H, NH3+), 7.74 (d, J3-2: 15.58 Hz, 1H, H3), 10.04 (m, 3H, NH)

Example 45

{2-[(2E)-3-(2-ethoxyphenyl)prop-2-enoyl]hydrazino}(imino)methane amino

The synthetic procedure of Example 30 is followed, starting with the compound of formula I of Example 43.
A yellow powder is obtained.
Melting point: 208° C.
1H NMR spectrum (DMSO d6): 1.39 (t, 3H, CH2CH3), 4.05 (q, 2H, CH2CH3), 6.53 (d, J2-3: 16.58 Hz, 1H, H2), 6.79 (m, 5H, NH—NH—C NH NH3+), 6.92 (m, 2H, H Ar), 7.20 (t, 1H, H Ar), 7.42 (d, J3-2: 16.50 Hz, 1H, H3), 7.49 (d, 1H, H Ar)

Example 46

{2-[(2E)-3-(2,5-dimethoxyphenyl)prop-2-enoyl]hydrazino}(imino)methane amino

The synthetic procedure of Example 30 is followed, starting with the compound of formula I of Example 44.
A yellow-white powder is obtained.
Melting point: 172° C.
1H NMR spectrum (DMSO d6): 3.71 (s, 3H, OCH3), 3.76 (s, 3H, OCH3), 6.60 (d, J2-3: 15.62 Hz, 1H, H2), 6.70 (m, 5H, NH—NH—C NH NH3+), 6.80, 6.82 (m, 2H, H Ar), 7.70 (s, 1H, H6'), 7.36 (d, J3-2: 15.60 Hz, 1H, H3)

Example 47 imino{2-[(2E)-3-(2-ethoxyphenyl)-2-prop-2-enoyl]hydrazino}methanaminium hydrochloride The synthetic procedure of Example 31 is followed, starting with the compound of formula I of Example 45.
A beige-colored powder is obtained.
Melting point: 212° C.
1H NMR spectrum (DMSO d6): 1.38 (t, 3H, CH2CH3), 4.12 (q, 2H, CH2CH3), 6.72 (d, J2-3: 15.62 Hz, 1H, H2), 7.00, 7.06 (m, 2H, H Ar), 7.36 (t, 1H, H Ar) 7.52 (d, 1H, H Ar), 7.60 (m, 4H, C NH NH3+), 7.78 (d, J3-2: 15.62 Hz, 1H, H3), 9.67 (s, 1H, NH), 10.37 (s, 1H, NH)

Example 48 imino{2-[(2E)-3-(2,5-dimethoxyphenyl)prop-2-enoyl]hydrazino}methanaminium hydrochloride The synthetic procedure of Example 31 is followed, starting with the compound of formula I of Example 46.

A beige-colored powder is obtained.
Melting point: 220° C.
1H NMR spectrum (DMSO d6): 3.72 (s, 3H, OCH3), 3.80 (s, 3H, OCH3), 6.78 (d, J2-3: 15.60 Hz, 1H, H2), 7.01 (m, 2H, H Ar), 7.07 (s, 1H, H6'), 7.64 (m, 4H, C NH NH3+), 7.72 (d, J3-2: 15.60 Hz, 1H, H3), 10.05 (s, 2H, NH—NH)

Examples of cosmetic compositions comprising the derivatives of the invention will now be given, each composition having been prepared with 1%, 2% and 5% of active substance.

| | % | Constituents (INCI nomenclature) | Category |
|---|---|---|---|
| Composition 1: O/W hydrophilic cream | | | |
| A | 2.00 | ceteareth-6, stearyl alcohol | nonionic surfactant |
| | 2.00 | ceteareth-25 | nonionic surfactant |
| | 4.00 | cetearyl alcohol | fatty alcohol |
| | 10.00 | cetearyl octanoate | nonionic surfactant |
| | 3.00 | glyceryl stearate | emollient, emulsifier |
| | 5.00 | petrolatum | conditioner, thickener, protective agent |
| B | 0.20 | EDTA | chelating agent |
| | 5.00 | propylene glycol | humectant, solvent |
| | qs | preserving agent | |
| | qs 100.00 | aqua | |
| C | 1.00 (2.00 and 5.00) | active substance: compound 29 | |

Heat phases A and B separately to 80° C. Add and mix the aqueous phase B with the fatty phase A and homogenize thoroughly. Cool the mixture to 40° C. and add phase C containing the active substance, with stirring, homogenize and continue stirring until the mixture has cooled to room temperature.

| | % | Constituents (INCI nomenclature) | Category |
|---|---|---|---|
| Composition 2: W/O lipophilic cream + anti UV-A mineral screening agent | | | |
| A | 5.00 | beeswax or beeswax substitute | emulsion stabilizer, conditioner, thickener |
| | 9.00 | paraffinum liquidum | emollient, protective agent |
| | 50.50 | petrolatum | mineral wax, conditioner, thickener, protective agent |
| | 0.50 | aluminum stearate | O/W emulsifying surfactant |
| | 10.00 | hydrogenated castor oil | conditioner, emulsifying surfactant |
| | 5.00 | CI 77891 (titanium dioxide) | opacifying white pigment |
| B | 0.7 | magnesium sulfate | vector, active agent support |
| | qs 100.00 | aqua | |
| | 1.00 (2.00 and 5.00) | active substance: Compound 29 | |

Mix the components of the oily phase A and heat to 60° C. The magnesium sulfate is dissolved in the water and the aqueous phase B is heated to 60° C.

Mix the two phases and add phase C containing the active substance, with stirring, homogenize and continue stirring until the mixture has cooled to room temperature.

| | % | Constituents (INCI nomenclature) | Category |
|---|---|---|---|
| | colspan="3" | Composition 3: Hydrophilic gel | |
| A | qs 100 | aqua | |
| | 0.2 | preserving agent | |
| | 1.00 (2.00 and 5.00) | active substance: compound 29 | |
| B | 24.00 | aqua | |
| | 0.1 | preserving agent | |
| | 0.75 | carbomer | aqueous-phase gelling agent |
| | qs pH = 6.5 | sodium hydroxide (N) | pH modifier |

In a first stage, prepare fractions A and B separately, and then, in a second stage, perform the gelation.

Preparation of fraction A: dissolve the preserving agent in distilled water at 50° C., then disperse the active substance therein with impeller stirring and leave the resulting mixture to cool to room temperature with planetary stirring.

Preparation of fraction B: dissolve the preserving agent in distilled water at 50° C., then disperse the carbomer therein with impeller stirring and leave the resulting mixture to cool to room temperature with planetary stirring.

To obtain the final gel, introduce phases B and C into phase A with impeller stirring and then homogenize the mixture with planetary stirring.

Composition 4: Lotion

| % | Constituents (INCI nomenclature) | Category |
|---|---|---|
| 0.60 | PEG-40-hydrogenated castor oil | conditioner, emulsifying surfactant |
| 10.00 | glycerol | humectant |
| 0.3 | preserving agent | |
| qs 100.00 | aqua | |
| 1.00 (2.00 and 5.00) | active substance: compound 29 | |

Dissolve the preserving agent in the water and the glycerol at 30° C. with stirring, then add the active substance with stirring, next add the PEG-40/hydrogenated castor oil mixture with stirring, and filter the resulting mixture.

Composition 5: Pomade

| % | Constituents (INCI nomenclature) | Category |
|---|---|---|
| 7.00 | petrolatum | mineral wax, conditioner, thickener, protective agent |
| 13.00 | microcrystalline wax | mineral wax, emollient, protective agent |
| qs 100.00 | paraffinum liquidum | emollient, protective agent |
| 1.00 | active substance: compound 29 | |

On a water bath, melt the mineral waxes in the liquid paraffin (paraffinum liquidum); when the waxes are melted, remove from the water bath and stir the mixture until it begins to set, then add the active substance and mix thoroughly.

Composition 6: Pomade

| % | Constituents (INCI nomenclature) | Category |
|---|---|---|
| 25.00 | beeswax | emulsion stabilizer, conditioner, thickener |
| qs 100.00 | mineral oil | conditioner, emollient |
| 1.00 (2.00 and 5.00) | active substance: compound 29 | |

On a water bath, melt the white wax (beeswax) in the liquid paraffin (paraffinum liquidum); when the wax is melted, remove the water bath and stir the mixture thoroughly until it begins to set, then add the active substance and mix thoroughly.

The anti-aging properties of a derivative according to the invention were evaluated by performing a comparative study of the anti-glycation activity of several compounds.

The products derived from glycation were revealed by observing the general morphology of the dermal and epidermal structures of explants thus treated and by immunolabeling of fibrillin-1, which is a protein serving as a structural component of microfibrils.

Procedure:

From an arm of a 32 year-old woman, 21 explants (about 10 mm in diameter) were prepared and placed under survival conditions in BEM specific medium (BIO-EC's Explants Medium).

The explants were divided into seven batches of three explants:

| Batch | No. of explants | Treatment | Sampling |
|---|---|---|---|
| T0 | 3 | None | D0 |
| T | 3 | None | D9 |
| R | 3 | Aminoguanidine at 0.15% | D9 |
| P | 3 | Compound 29 at 1% | D9 |
| T MG | 3 | Methylglyoxal | D9 |
| R MG | 3 | Aminoguanidine at 0.15% + Methylglyoxal | D9 |
| P MG | 3 | Compound 29 at 1% + Methylglyoxal | D9 |

Aminoguanidine is an anti-glycation compound commonly used in the prior art and constitutes the reference in this study.

Methylglyoxal is a glycation agent.

Procedure

Methylglyoxal was incorporated into the survival medium on D3, D5 and D7.

Compound 29 and the reference, aminoguanidine, were applied topically at a rate of 2 mg per explant on D0, D3, D5 and D7.

The controls (batches T0 and T) received no treatment.

On D0, the three explants of batch T0 were sampled and divided into two. One half was fixed with buffered formaldehyde and the other half was frozen at −80° C. On D9, three explants from each batch were sampled and treated in the same manner.

After 24 hours of fixing in the buffered formaldehyde, the samples were dehydrated and impregnated with paraffin using a Leica 1020 dehydration robot. They were embedded using a Leica EG 1160 coating station. 5 μm slices were produced using a Minot Leica RM 2125 microtome and bonded to Superfrost® histological glass slides.

The observation of the general morphology was performed on paraffin slices after staining with Goldner-variant Masson's trichrome.

The fibrillin-1 was labeled using an anti-fibrillin-1 monoclonal antibody, clone 11.C1.3, from Neo Markers (ref. MS 231), performed on mice at a 1/200 dilution for 1 hour at room temperature with a Vectastain RTU Universal VECTOR avidin/biotin amplifier system and revealed with FITC. The nuclei were stained with propidium iodide. The labeling was quantified by image analysis measurements with the Q-WIN Leica system.

Results

On D0, the morphology of the explants of the control batch T0 is such that the stratum corneum is relatively thin, quite compact, quite markedly keratinized at the surface and very markedly at its base. The epidermis shows 4 to 5 cellular beds with very good morphology. The relief of the dermo-epidermal junction is very sharp. The papillary dermis presents collagen with quite thick fibers forming a quite dense network. It is correctly cellularized.

On D9, on the explants of the untreated batch T, the general morphology is similar to that observed on D0.

Irrespective of the product applied to the explants of the treated batches, the general morphology is sparingly modified, with parakeratosis more or less present and more or less pronounced basal spongiosis.

As regards fibrillin-1, on D0, on the explants of the untreated batch T0, the labeling is sharp, very regular on oxytalane fibers that are quite long and highly branched along the dermo-epidermal junction. It is very moderate on the elastic fibers of the subjacent network in the papillary dermis.

On D9, on the explants of the untreated batch T, the expression of fibrillin-1 is slightly greater than that observed on D0: the labeling is very sharp and regular.

On batch R, treated with aminoguanidine, the expression of fibrillin-1 is similar to that observed on the untreated control batch T.

On batch P treated with the guanidine derivative of the invention, the expression of fibrillin-1 is similar to that observed on the untreated control batch T.

After incorporation of methylglyoxal, to the batch T MG, the expression of fibrillin-1 is moderately decreased, and quite irregular, relative to that of the control batch T without methylglyoxal.

On batch R MG treated with aminoguanidine in the presence of methylglyoxal, the expression of fibrillin-1 is very sharp and greater than that observed on the control batch T MG with methylglyoxal.

On batch P MG treated with the guanidine derivative of the invention in the presence of methylglyoxal, the expression of fibrillin-1 is very sharp and greater than that observed on the control batch T MG with methylglyoxal.

Furthermore, the image analysis results are collated in the table below.

Fibrillin-1 (% of Surface Area Under the Dermo-Epidermal Junction)

|  | D0 Mean | D0 Standard deviation | D9 without methylglyoxal Mean | D9 without methylglyoxal Standard deviation | D9 with methylglyoxal Mean | D9 with methylglyoxal Standard deviation |
|---|---|---|---|---|---|---|
| Control | 15.0 | 2.8 | 23.7 | 5.4 | 18.2 | 3.4 |
| r |  |  | 28.3 | 7.2 | 21.0 | 5.3 |
| p |  |  | 21.53 | 5.09 | 27.7 | 4.6 |

In the control batch T MG, the incorporation of methylglyoxal to the survival medium induces a 23% decrease in the percentage of surface area occupied by fibrillin-1 under the dermo-epidermal junction, relative to the control batch T without methylglyoxal.

In batch R MG treated with aminoguanidine, the incorporation of methylglyoxal to the survival medium induces a 12% decrease in the percentage of surface area occupied by fibrillin-1 under the dermo-epidermal junction, relative to the control batch T without methylglyoxal.

In batch P MG treated with the guanidine derivative of the invention, the incorporation of methylglyoxal to the survival medium induces a 17% increase in the percentage of surface area occupied by fibrillin-1 under the dermo-epidermal junction, relative to the control batch T without methylglyoxal.

Thus, methylglyoxal induces a marked decrease in the expression of fibrillin-1 in the untreated batch T, and treatment with aminoguanidine makes it possible to reduce this decrease by 49%, whereas treatment with the guanidine derivative of the invention totally inhibits the action of methylglyoxal.

The invention claimed is:

1. Guanidine derivatives, salts and isomers in the cinnamic acid series, of general formula (I) below:

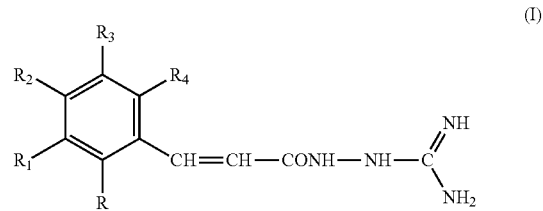

in which:

R1 and R2 together form a group OCH2O, and

R, R3 and R4 each represent a hydrogen atom.

2. Salt according to claim 1, which is an addition salt of a mineral acid selected from HCl, HBr and H2SO4, or an addition salt of an organic acid selected from methanesulfonic acid, benzoic acid, salicylic acid, lactic acid, citric acid, D or L malic acid, D glucuronic acid and hyaluronic acid.

3. Process for preparing the derivatives, isomers and salts according to claim 1, comprising:

(i) the reaction of 3,5-dimethylpyrazole-1-carboxamidine nitrate with a compound of general formula (III) below:

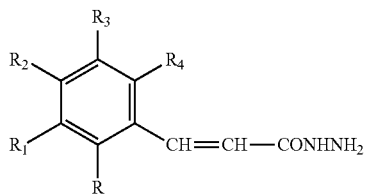

(III)

to obtain the nitrate of a compound of formula (I), (ii) the optional basification of the nitrate obtained in step (i), to obtain the compound of formula (I), and (iii) the optional salification of the compound of formula (I) obtained in step (ii) with a suitable mineral or organic acid.

4. Process according to claim 3, further comprising reacting of hydrazine with a compound of general formula (II) below:

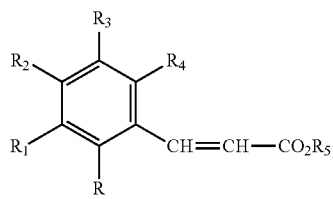

(II)

in which $R_5$ represents a C1-C4 alkyl group,
to obtain the compound of formula (III).

5. Process according to claim 4, further comprising:

(iv) reacting of 1-(methylsulfonyl)benzotriazole with a compound of general formula (IV) below:

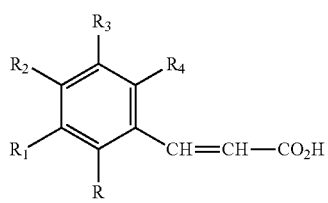

(IV)

to obtain a compound of general formula (V) below:

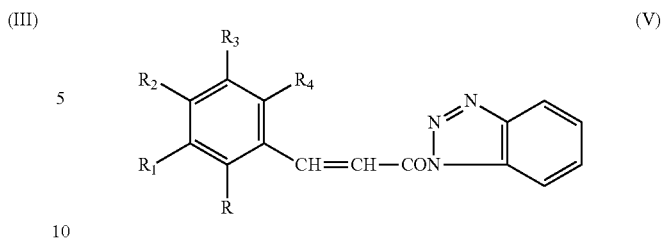

(V)

, and (v) reacting of the compound of formula (V) obtained in step (iv) with hydrazine to obtain the compound of formula (III).

6. Cosmetic composition comprising at least one derivative, isomer or salt according to claim 1 and a cosmetically acceptable vehicle.

7. Salt in the cinnamic acid series, of general formula (I) below:

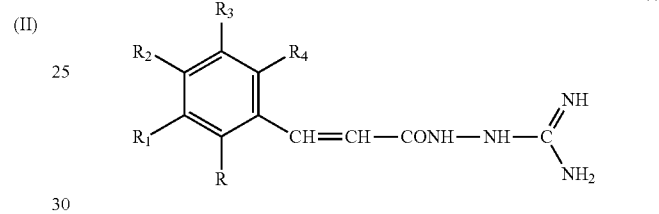

(I)

in which:
R represents a hydrogen atom or a C1-C4 alkoxy group,
$R_1$ represents a hydrogen atom, a C1-C4 alkoxy group, a group $NO_2$ or a group OH,
$R_2$ represents a hydrogen atom, a C1-C4 alkoxy group or a group OH,
$R_1$ and $R_2$ may also together form a group $OCH_2O$,
$R_3$ represents a hydrogen atom or a C1-C4 alkoxy group, and
$R_4$ represents a hydrogen atom, wherein
the salt is an addition salt of a mineral acid selected from HCl, HBr and $H_2SO_4$, or an addition salt of an organic acid selected from methanesulfonic acid, benzoic acid, salicylic acid, lactic acid, citric acid, D or L malic acid, D glucuronic acid and hyaluronic acid.

8. Salt according to claim 7, of formula (I) in which the set (R, R1, R2, R3, R4) is chosen from the group consisting of (H, H, H, H, H), (H, $NO_2$, H, H, H), (C1-C4 alkoxy, H, H, H, H) and (H, C1-C4 alkoxy, OH, H, H).

* * * * *